(12) United States Patent
Hsieh

(10) Patent No.: US 8,178,335 B2
(45) Date of Patent: May 15, 2012

(54) INTRACELLULAR PRODUCTION OF A NUCLEASE

(75) Inventor: Pei-Chung Hsieh, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/072,980

(22) Filed: Mar. 28, 2011

(65) Prior Publication Data

US 2011/0189753 A1  Aug. 4, 2011

Related U.S. Application Data

(63) Continuation of application No. 11/660,110, filed as application No. PCT/US2005/028739 on Aug. 12, 2005, now Pat. No. 7,935,509.

(60) Provisional application No. 60/601,309, filed on Aug. 13, 2004.

(51) Int. Cl.
*C07H 21/00* (2006.01)
*C12N 15/00* (2006.01)
*C12N 1/21* (2006.01)
*C12N 5/10* (2006.01)
*C12P 21/00* (2006.01)
*C12N 9/16* (2006.01)

(52) U.S. Cl. .................. 435/196; 435/252.3; 435/320.1; 435/69.1; 435/69.7; 435/325; 536/23.2

(58) Field of Classification Search ................. 435/69.1, 435/320.1, 18, 6, 69.7, 196, 199, 252.3, 325; 536/23.2

See application file for complete search history.

(56) References Cited

U.S. PATENT DOCUMENTS 5,173,418 A 12/1992 Molin et al.
2002/0012982 A1 1/2002 Blakesley et al.

OTHER PUBLICATIONS

Ball_etal_Gene_57_183-192_1987.
Branden_etalintro_Prot_Struct_Garland_Pub_NY_247_1991.
Seffernick_etal_J_Bacteriol_183_8_2405-2410_2001.
Shortle_etal_Biochemistry_28_936-944_1989.
Eaves_etal_J_Bactenol_85_273-278_1963.
Friedhoff_etal_Protein_Expr_Purif 5_1_37-43_1994.
Myung_etal_J_Bacteriol_177_3_497-501_1995.
Toksoy_etal_Biotech_Tech_13_803-808_1999.
Von_Heijne_Nucleic_Acids_Research_14_11_4683-4690_1986.
Witkowski_etal_Biochemistry_38_11643-11650_1999.
Filimonova_etal_Biochem_Mol_Biol_Int_33_6_1229-1236_1994.

*Primary Examiner* — Delia Ramirez
(74) *Attorney, Agent, or Firm* — New England Biolabs, Inc; Harriet M. Strimpel

(57) ABSTRACT

Methods and compositions are provided that relate to obtaining a recombinant DNA and RNA cleaving nuclease. This involves the over-expression of a fusion protein between maltose-binding protein and a truncated nuclease in a soluble form in the cytoplasm of a host cell from which it can be readily extracted.

9 Claims, 5 Drawing Sheets

Figure 4a (SEQ ID NO:1)

ATGAAAATCGAAGAAGGTAAACTGGTAATCTGGATTAACGGCGATAAAGGCTATAACGGTCTCGCTGAAGTCGGTA
AGAAATTCGAGAAAGATACCGGAATTAAAGTCACCGTTGAGCATCCGGATAAACTGGAAGAGAAATTCCCACAGGT
TGCGGCAACTGGCGATGGCCCTGACATTATCTTCTGGGCACACGACCGCTTTGGTGGCTACGCTCAATCTGGCCTG
TTGGCTGAAATCACCCCGGACAAAGCGTTCCAGGACAAGCTGTATCCGTTTACCTGGGATGCCGTACGTTACAACG
GCAAGCTGATTGCTTACCCGATCGCTGTTGAAGCGTTATCGCTGATTTATAACAAAGATCTGCTGCCGAACCCGCC
AAAAACCTGGGAAGAGATCCCGGCGCTGGATAAAGAACTGAAAGCGAAAGGTAAGAGCGCGCTGATGTTCAACCTG
CAAGAACCGTACTTCACCTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTTGACCTGATTAAAAACAA
ACACATGAATGCAGACACCGATTACTCCATCGCAGAAGCTGCCTTTAATAAAGGCGAAACAGCGATGACCATCAAC
GGCCCGTGGGCATGGTCCAACATCGACACCAGCAAAGTGAATTATGGTGTAACGGTACTGCCGACCTTCAAGGGTC
AACCATCCAAACCGTTCGTTGGCGTGCTGAGCGCAGGTATTAACGCCGCCAGTCCGAACAAAGAGCTGGCAAAAGA
GTTCCTCGAAAACTATCTGCTGACTGATGAAGGTCTGGAAGCGGTTAATAAAGACAAACCGCTGGGTGCCGTAGCG
CTGAAGTCTTACGAGGAAGAGTTGGCGAAAGATCCACGTATTGCCGCCACTATGGAAAACGCCCAGAAAGGTGAAA
TCATGCCGAACATCCCGCAGATGTCCGCTTTCTGGTATGCCGTGCGTACTGCGGTGATCAACGCCGCCAGCGGTCG
TCAGACTGTCGATGAAGCCCTGAAAGACGCGCAGACTAATTCGAGCTCGAACAACAACAACAATAACAATAACAAC
AACCTCGGGATCGAGGGAAGGGCCGACACGCTCGAATCCATCGACAACTGCGCGGTCGGCTGTCCGACCGGCGGCA
GCAGCAACGTGTCTATCGTGCGTCATGCTTATACGTTGAACAACAACAGCACCACCAAGTTCGCCAACTGGGTGGC
CTATCACATCACCAAAGACACGCCGGCCAGCGGCAAGACGCGCAACTGGAAAACCGATCCGGCGCTCAACCCGGCG
GATACGTTGGCGCCCGCCGATTACACCGGCGCCAACGCCGCGCTGAAGGTCGATCGCGGTCATCAGGCGCCGCTGG
CCTCGCTGGCGGGCGTCTCCGACTGGGAATCGTTGAACTACCTGTCCAACATCACGCCGCAAAAGTCCGATCTGAA
CCAGGGCGCCTGGGCGCGGCTGGAAGATCAGGAACGCAAGCTGATCGATCGCGCCGATATATCCTCGGTCTATACC
GTGACCGGGCCGCTGTATGAGCGCGATATGGGCAAACTGCCGGGCACGCAGAAAGCGCACACCATCCCCAGCGCCT
ACTGGAAGGTGATTTTCATCAACAACAGCCCGGCGGTGAACCACTATGCCGCCTTCCTGTTCGACCAGAACACGCC
GAAGGCGGCCGATTTCGACCAATTCCGGGTGACGGTGGACGAGATCGAGAAACGCACCGGCCTGATCATCTGGGCC
GGTCTGCCGGACGACGTGCAGGCTTCGCTGAAGAGCAAACCGGGCGTGCTGCCGGAGTTGATGGGCTGCAAAAACT
GA

Figure 4b (SEQ ID NO:2)

MKIEEGKLVIWINGDKGYNGLAEVGKKFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNPPKTWEEIPALDKELKAKGKSALMFNL
QEPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAVA
LKSYEEELAKDPRIAATMENAQKGEIMPNIPQMSAFWYAVRTAVINAASGRQTVDEALKDAQTNSSSNNNNNNNNN
NLGIEGRADTLESIDNCAVGCPTGGSSNVSIVRHAYTLNNNSTTKFANWVAYHITKDTPASGKTRNWKTDPALNPA
DTLAPADYTGANAALKVDRGHQAPLASLAGVSDWESLNYLSNITPQKSDLNQGAWARLEDQERKLIDRADISSVYT
VTGPLYERDMGKLPGTQKAHTIPSAYWKVIFINNSPAVNHYAAFLFDQNTPKAADFDQFRVTVDEIEKRTGLIIWA
GLPDDVQASLKSKPGVLPELMGCKN

Figures 8A, 8B:
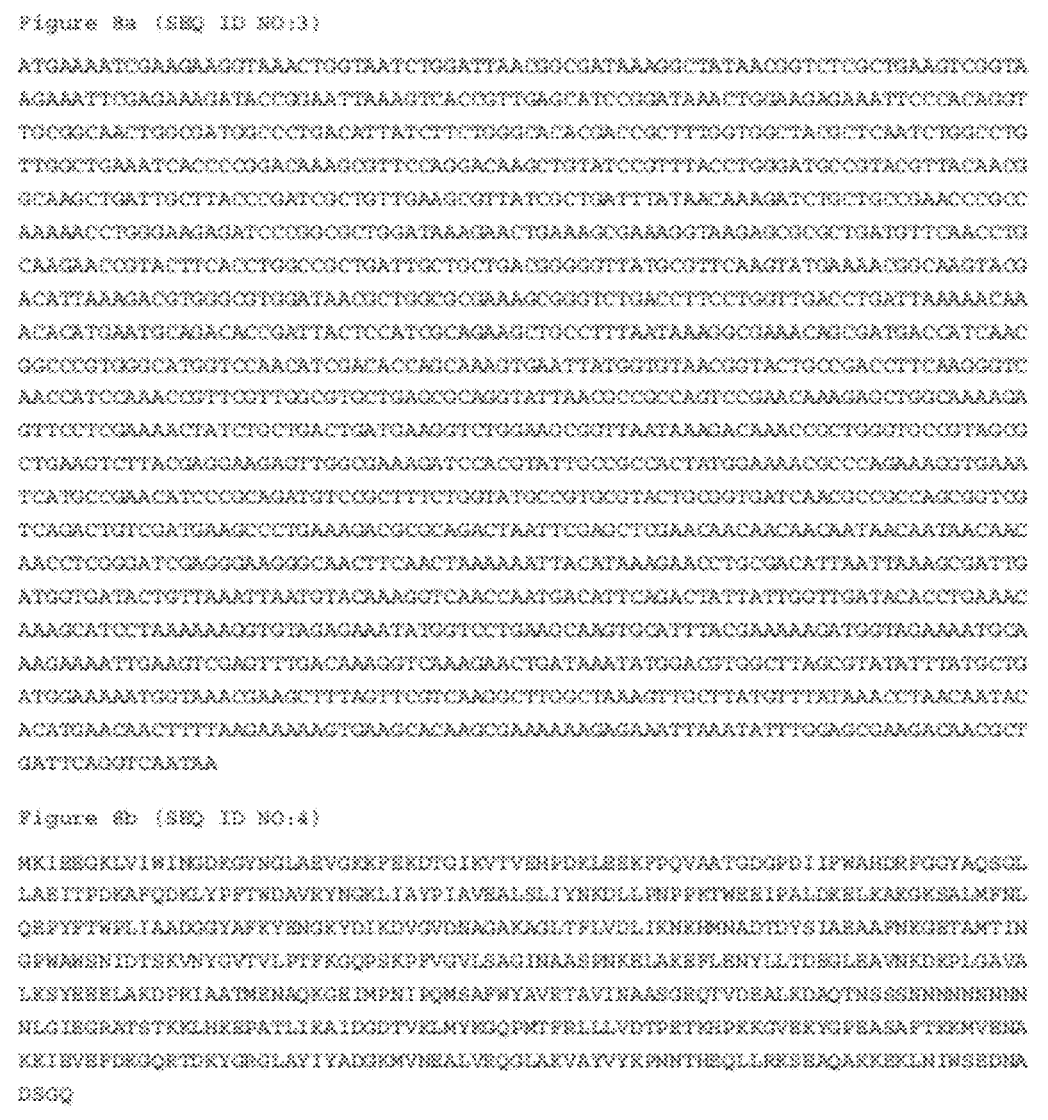

Figure 8a (SEQ ID NO:3)

Figure 1:
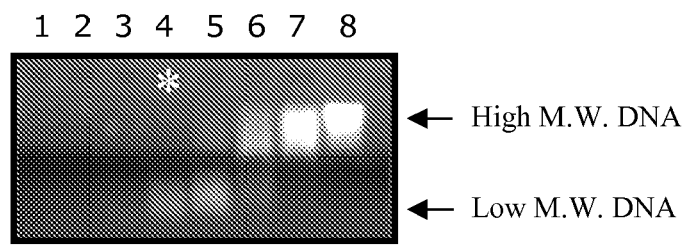

ATGAAAATCGAAGAAGGTAAACTGGTAATCTGGATTAACGGCGATAAAGGCTATAACGGTCTCGCTGAAGTCGGTA
AGAAATTCGAGAAAGATACCGGAATTAAAGTCACCGTTGAGCATCCGGATAAACTGGAAGAGAAATTCCCACAGGT
TGCGGCAACTGGCGATGGCCCTGACATTATCTTCTGGGCACACGACCGCTTTGGTGGCTACGCTCAATCTGGCCTG
TTGGCTGAAATCACCCCGGACAAAGCGTTCCAGGACAAGCTGTATCCGTTTACCTGGGATGCCGTACGTTACAACG
GCAAGCTGATTGCTTACCCGATCGCTGTTGAAGCGTTATCGCTGATTTATAACAAAGATCTGCTGCCGAACCCGCC
AAAAACCTGGGAAGAGATCCCGGCGCTGGATAAAGAACTGAAAGCGAAAGGTAAGAGCGCGCTGATGTTCAACCTG
CAAGAACCGTACTTCACCTGGCCGCTGATTGCTGCTGACGGGGGTTATGCGTTCAAGTATGAAAACGGCAAGTACG
ACATTAAAGACGTGGGCGTGGATAACGCTGGCGCGAAAGCGGGTCTGACCTTCCTGGTTGACCTGATTAAAAACAA
ACACATGAATGCAGACACCGATTACTCCATCGCAGAAGCTGCCTTTAATAAAGGCGAAACAGCGATGACCATCAAC
GGCCCGTGGGCATGGTCCAACATCGACACCAGCAAAGTGAATTATGGTGTAACGGTACTGCCGACCTTCAAGGGTC
AACCATCCAAACCGTTCGTTGGCGTGCTGAGCGCAGGTATTAACGCCGCCAGTCCGAACAAAGAGCTGGCAAAAGA
GTTCCTCGAAAACTATCTGCTGACTGATGAAGGTCTGGAAGCGGTTAATAAAGACAAACCGCTGGGTGCCGTAGCG
CTGAAGTCTTACGAGGAAGAGTTGGCGAAAGATCCACGTATTGCCGCCACTATGGAAAACGCCCAGAAAGGTGAAA
TCATGCCGAACATCCCGCAGATGTCCGCTTTCTGGTATGCCGTGCGTACTGCGGTGATCAACGCCGCCAGCGGTCG
TCAGACTGTCGATGAAGCCCTGAAAGACGCGCAGACTAATTCGAGCTCGAACAACAACAACAATAACAATAACAAC
AACCTCGGGATCGAGGGAAGGGCAACTTCAACTAAAAAATTACATAAAGAACCTGCGACATTAATTAAAGCGATTG
ATGGTGATACTGTTAAATTAATGTACAAAGGTCAACCAATGACATTCAGACTATTATTGGTTGATACACCTGAAAC
AAAGCATCCTAAAAAAGGTGTAGAGAAATATGGTCCTGAAGCAAGTGCATTTACGAAAAAAATGGTAGAAAATGCA
AAGAAAATTGAAGTCGAGTTTGACAAAGGTCAAAGAACTGATAAATATGGACGTGGCTTAGCGTATATTTATGCTG
ATGGAAAAATGGTAAACGAAGCTTTAGTTCGTCAAGGCTTGGCTAAAGTTGCTTATGTTTATAAACCTAACAATAC
ACATGAACAACTTTTAAGAAAAAGTGAAGCACAAGCGAAAAAAGAGAAATTAAATATTTGGAGCGAAGACAACGCT
GATTCAGGTCAATAA

Figure 8b (SEQ ID NO:4)

MKIEEGKLVIWINGDKGYNGLAEVGKKFEKDTGIKVTVEHPDKLEEKFPQVAATGDGPDIIFWAHDRFGGYAQSGL
LAEITPDKAFQDKLYPFTWDAVRYNGKLIAYPIAVEALSLIYNKDLLPNPPKTWEEIPALDKELKAKGKSALMFNL
QEPYFTWPLIAADGGYAFKYENGKYDIKDVGVDNAGAKAGLTFLVDLIKNKHMNADTDYSIAEAAFNKGETAMTIN
GPWAWSNIDTSKVNYGVTVLPTFKGQPSKPFVGVLSAGINAASPNKELAKEFLENYLLTDEGLEAVNKDKPLGAVA
LKSYEEELAKDPRIAATMENAQKGEIMPNIPQMSAFWYAVRTAVINAASGRQTVDEALKDAQTNSSSNNNNNNNNN
NLGIEGRATSTKKLHKEPATLIKAIDGDTVKLMYKGQPMTFRLLLVDTPETKHPKKGVEKYGPEASAFTKKMVENA
KKIEVEFDKGQRTDKYGRGLAYIYADGKMVNEALVRQGLAKVAYVYKPNNTHEQLLRKSEAQAKKEKLNIWSEDNA
DSGQ

INTRACELLULAR PRODUCTION OF A NUCLEASE

CROSS REFERENCE

This application is a continuation of U.S. patent application Ser. No. 11/660,110 filed Feb. 12, 2007, which is a §371 Application of PCT Application No. PCT/US05/28739 filed Aug. 12, 2005, which claims priority from U.S. Provisional Application No. 60/601,309 filed Aug. 13, 2004, herein incorporated by reference.

BACKGROUND

Nucleases are useful reagents for removing nucleic acids from protein preparations. All cells contain nucleases. Some nucleases can degrade both DNA as well as RNA in their double- and single-stranded forms. Some of nucleases degrade either DNA or RNA. Some of nucleases have more specific substrates, for example, single-stranded DNA. Reagent nucleases have been isolated either from the native host or as recombinant proteins. A problem encountered with cloning nucleases, which cleave both DNA and RNA, is that these proteins become toxic to host cells such as *E. coli* if overexpression is attempted using *E. coli* or other hosts. The toxicity effect can be ameliorated to some extent by causing the host cell either to efficiently secret the nuclease or to sequester the nuclease in an inclusion body in the host cell. Both methods have some disadvantages. Obtaining purified nuclease from media requires handling large volumes, which can be laborious. Release of nucleases from inclusion bodies in lysed cells requires denaturing quantities of urea (for example 6M urea) after which the nuclease has to be renatured to restore its enzymatic activity. It would therefore be desirable to have methods of obtaining nucleases in a simple way.

Descriptions of certain nucleases and their preparation by cloning are provided by Eaves et al. (*J. Bacteriol.* 85:273-8 (1963)), Filimonova et al. (*Biochem. Mol. Biol. Int.* 33(6): 1229-36 (1994)), Ball et. al. (*Gene* 57(2-3):183-92 (1987), Molin et. al. (U.S. Pat. No. 5,173,418), and Friedhoff et al. (*Protein Expr. Purif.* 5(1):37-43 (1994)).

SUMMARY

In an embodiment of the invention, a modified nuclease in the form of a fusion protein is provided. This fusion protein contains a maltose-binding protein (MBP) fused to the nuclease such that the fusion protein is capable of being over-expressed in a host cell without causing lethality. A feature of the modified nuclease is that more than 80% of the expressed nuclease fusion protein is dispersed in the cytoplasm of the host cell. Examples of modified nuclease are provided from *Serratia marcescens* (*S. marcescens*) and *Staphylococcus aureus* (*S. aureus*).

The modified nuclease may be further characterized as truncated wherein the truncation corresponds to the removal of substantially all of the signal sequence.

In another embodiment of the invention, a DNA segment is provided for encoding the MBP-nuclease fusion protein.

In a further embodiment of the invention, a host cell is provided that is capable of expressing the nuclease-MBP fusion protein.

In a further embodiment of the invention, a method is provided for obtaining a nuclease for cleaving DNA and RNA, that includes the steps of (a) obtaining a DNA segment encoding a nuclease substantially lacking a signal sequence and a MBP; (b) expressing the DNA segment within a host cell to produce a significant concentration of nuclease fusion protein in the cytoplasm; (c) lysing the host cell; and (d) obtaining the isolated DNA and RNA nuclease.

In an example of the method, the nucleases are encoded by the DNAs derived from *S. marcescens* or *S. aureus*.

In a further embodiment of the invention, a method for preparing a non-viscous extract of a prokaryotic cell is provided having the steps of: adding MBP-nuclease fusion protein, decanoyl-N-methylglucamide and a lysozyme to a cell pellet or cell suspension; and preparing the non-viscous extract from the prokaryotic cells.

LIST OF FIGURES

FIG. 1 shows an assay for nuclease activity using lambda-DNA substrate. A 2-fold serial dilution of the *S. marcescens* nuclease fused to MBP is used in each lane to digest 1 µg of λ genomic DNA. * symbol in Lane 4 is the amount of enzyme defined as one unit of nuclease activity.

Figure 2:
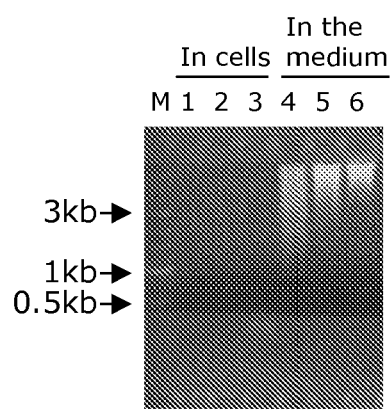

FIG. 2 shows that expressed *S. marcescens* nuclease fused to MBP remains in the *E. coli* cytoplasm and is not secreted. Lanes are as follows:
Lane M is the DNA marker;
Lanes 1, 2 and 3 show the DNA nuclease activity from sonicated cells with 1×, 10× and 100× dilution;
Lanes 4, 5 and 6 show the enzymes from cell-free culture with 1×, 10× and 100× dilution.

Figure 3:
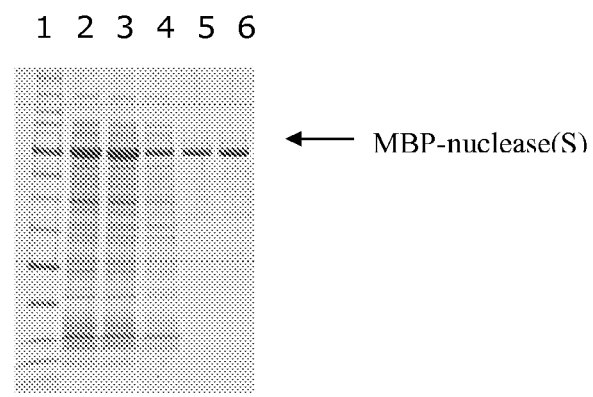

FIG. 3 shows that the amount of expressed *S. marcescens* nuclease fused to MBP (MBP-nuclease(S)) in the crude extracts of *E. coli* are similar. Lanes are as follows:
Lane 1 is protein marker (New England Biolabs, Inc., Ipswich, Mass.—NEB #P7702);
Lane 2 is a crude extract from ER2683;
Lane 3 is a crude extract from ER1992;
Lane 4 shows the unbound fraction of a crude extract after fractionation on an amylose column;
Lanes 5 and 6 show the eluted *S. marcescens* nuclease fused to MBP after addition of 10 mM maltose to the column.

FIG. 4 shows (a) the DNA sequence (SEQ ID NO:1) and (b) the amino acid sequence (SEQ ID NO:2) of a non-secreted form of *S. marcescens* nuclease fused to MBP.

Figure 5:
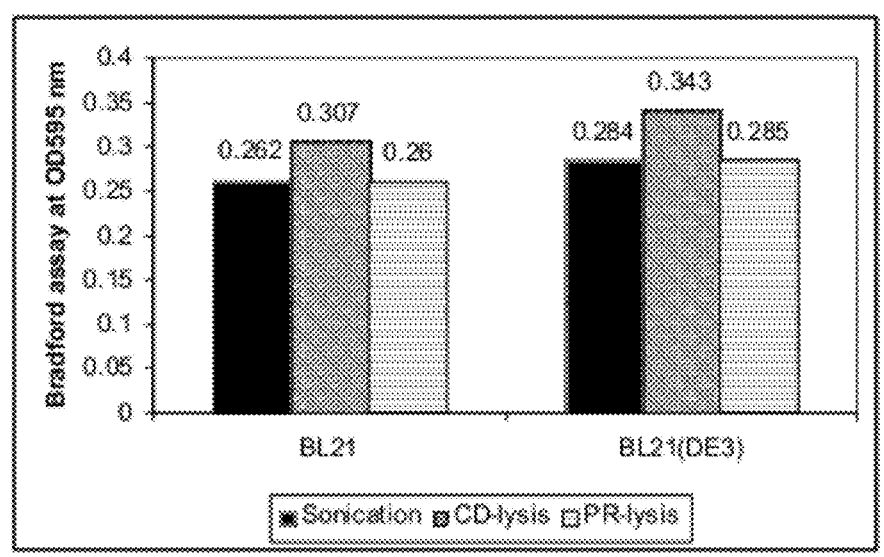

FIG. 5 shows the use of *S. marcescens* nuclease fused to MBP for the detergent-based cell-lysis reaction. Two *E. coli* strains were lysed by three different methods: sonication, CD-lysis reagent and PR-lysis reagent. Each method released similar total amount of proteins in the cell lysate as evidenced by the Bradford protein assay.

Figure 6:
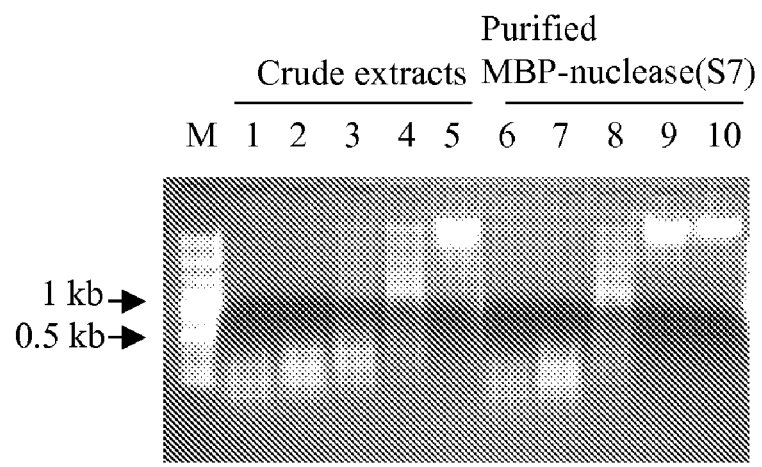

FIG. 6 shows that the expressed *S. aureus* nuclease fused to MBP (MBP-nucleases(S7)) is substantially non-secreted. The *E. coli* crude extracts, which were prepared from the harvested cells followed by sonication and centrifugation, were diluted 3-fold in serial reactions and showed to contain the nuclease activities in lanes 1 to 5. Lanes 6-10 showed the nuclease activity of purified fusion enzymes from an amylose column with 3-fold serial dilution from lanes 1-5 to lanes 6-10.

Figure 7:
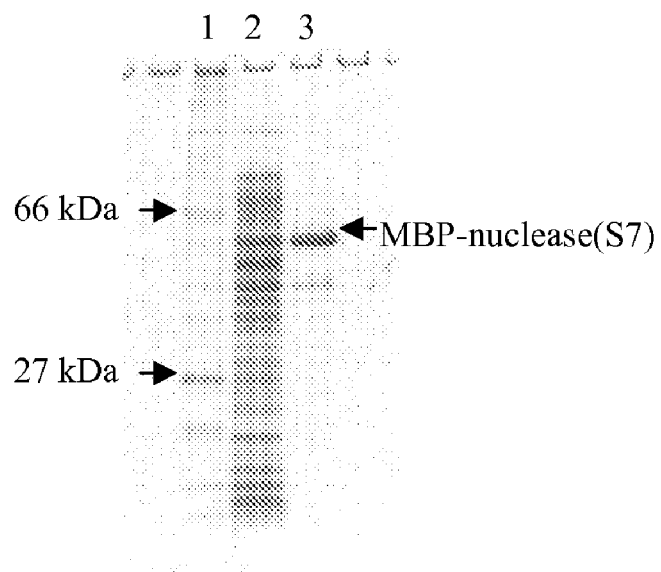

FIG. 7 shows that substantially all *S. aureus* nuclease fused to MBP is obtained in the crude extracts of *E. coli* (ER1992). Lanes are as follows:
Lane 1 is a protein marker (New England Biolabs, Inc., Ipswich, Mass., #P7702);
Lane 2 shows the crude extracts from ER1992;
Lane 3 shows the purified *S. aureus* nuclease fused to MBP eluted by addition of 10 mM maltose to the column.

FIG. 8 shows (a) the DNA sequence (SEQ ID NO:3) and (b) the amino acid sequence (SEQ ID NO:4) of a non-secreted form of *S. aureus* nuclease fused to MBP.

DESCRIPTION

An improved method for obtaining a nuclease capable of cleaving both DNA and RNA has been developed. The method involves intracellular over-production of the nuclease in the form of a fusion protein having substantially reduced toxicity. In one embodiment, reduced toxicity is achieved by fusion of the nuclease to MBP. The fusion may be made by removing a substantial portion of the signal peptide portion of the nuclease and adding MBP. For example, the signal sequence can be substituted for the MBP.

The portion of the signal sequence from the nuclease protein that should be removed is not required to be a precise number of amino acids. For example, whereas the length of the signal sequence may be 21 amino acids (von Heijne, G. *Nucleic Acids. Res.* 14(11):4683-90 (1986)), as few as 19 amino acids in the signal peptide can be removed. Cell survival is improved by substituting substantially all the signal sequence with MBP.

The addition of the MBP moiety in the nuclease fusion protein results in a nuclease that can be trapped in the cytoplasm of the host cell in the soluble form and at high expression levels. The fusion protein can then be purified from lysed cells by means of amylose affinity chromatography in a simple purification step (pMal protein fusion and purification system described in New England Biolabs, Inc., Ipswich, Mass. catalog). Using this approach, over-expression of soluble, non-secreted nucleases in the cytoplasm of *E. coli* region yielded >25 mg/L of nuclease.

The formation of an MBP-nuclease fusion protein can be achieved by ligating the DNA coding for the nuclease absent substantially all of the coding region for the signal sequence and the DNA coding for MBP. The DNA segment can be inserted into any suitable commercially available cloning vector for growing in an appropriate host cell. There is no known limitation on the type of prokaryotic or eukaryotic host cells used for this purpose. In an embodiment of the invention, the nuclease is over-expressed which here refers to being capable of being visualized as a distinct band on a 10%-20% polyacrylamide gel.

The present method is suitable for any DNA and RNA cleaving nuclease encoded by prokaryotic, eukaryotic or archeal cells or functional variants or derivatives of these nucleases. The method is exemplified here by two examples: *S. marcescans* nuclease and *S. aureus* nuclease.

One use for nucleases as reagents is in breaking up prokaryotic cells that contain proteins of interest. Cells can be broken up by non-mechanical means such as with detergents. For prokaryotic cells that lack a nuclear membrane, lysis of cells results in production of a high viscosity mixture because of released nucleic acid. The addition of a nuclease that digests DNA and RNA results in a clarified protein extract permitting further purification. In a preferred embodiment, a method is provided here for using a specific detergent together with a nuclease and lysozyme. Any type of lysozyme can be used such as chicken, T7 or T4 lysozyme.

The references cited above and below as well as U.S. Provisional Application Ser. No. 60/601,309 filed Aug. 13, 2004 are herein incorporated by reference.

EXAMPLES

Example 1

Over-Expression of *S. marcescens* Nuclease Fused to MBP

Bacterial Strain and Growth

The *E. coli* strains ER2683 and ER1992 were used to propagate plasmids and express fusion proteins. These strains are characterized by the following genotypes: ER2683 (MM294 background) F' proA+B+ lacIq DlacZM15 miniTn10 (KanR) fhuA2 D(lacI-lacA)200 glnV44 e14– rfbD1? relA1? endA1 spoT1? thi-1 D(mcrC-nmr)114::IS10 ER1992 (MM294 background) D(argF-lac)U169 glnV44 mcr-67 rfbD1? relA1? endA1 dinD2::MudI1734 (KanR, lacZ+) spoT1? thi-1 D(mcrC-nmr)114::IS10.

Plasmid pMAL-c2X (New England Biolabs, Inc., Ipswich, Mass.) was used to clone the nuclease DNA (SEQ ID NO:1) with expression controlled by $P_{tac}$ promotor and the laI repressor. Normal growth medium was LB supplemented with 100 µg/ml Amp and 0.2% (w/v) of glucose. *E. coli* was grown at 37° C.

A single bacterial colony with a red color was isolated from Japanese beetles by crushing beetles and spreading a sample on an LB plate at 30° C. The strain of *S. marcescens* was identified according to the sequences of 16S ribosomal DNA (bp27-1492). This isolate was used to obtain the nuclease gene as described below.

Preparation of Genomic DNA

A one ml preparation of an overnight culture at 30° C. of *S. marcescens* cells was centrifuged and resuspended in 100 µl of $H_2O$ containing 0.2% NP-40 and 10 mM EDTA. The solution was incubated at 100° C. for 10 min to release the genomic DNA of *S. marcescens* and to serve as a template for PCR.

Cloning of Nucleases from *S. marcescens*

In order to amplify the nuclease by Vent DNA polymerase (New England Biolabs, Inc., Ipswich, Mass., NEB #M0254S), two primers were synthesized: 5'-GCCGA-CACGCTCGAATCCATCGACAAC-3' (SEQ ID NO:5) and 5'-AGTCGGATCCTCAGTTTTTGCAGCCCAT-CAACTCCGG-3' (SEQ ID NO:6). The PCR product was 741 bp and was cut with BamHI. Gel-purified BamHI-cut PCR products were kinased and cloned into the XmnI/BamHI region of pMAL-c2X vector, followed by transforming into ER1992. Two out of 18 colonies were found to carry the nuclease activity according to the assay below. The isolated plasmids containing the nuclease gene were sequenced using the ABI Bigdye terminator V3.1 sequencing kit (Applied Biosystems, Foster City, Calif.). DNA sequence confirmed that one of the clones carries the gene of *S. marcescens* nuclease with DNA nuclease activity. This plasmid was named pMAL-c2X-nuclease(S) (S for *S. marcescens*).

New transformants (ER1992 or ER2683 as hosts) carrying pMAL-c2X-nuclease(S) plasmid were grown at 37° C. on an LB plate with Amp. A single colony was inoculated into 2 ml LB+ glucose and grown overnight. Two hundred microliters of the overnight culture were added to fresh 10 ml of LB+Amp+glucose medium and grown to a density of $OD_{600nm}=1.0$, followed by addition of 1 mM of IPTG. After two hours induction, cells were harvested by centrifugation.

Assay for Nuclease Activity

The nuclease activity assay buffer used here contains 50 mM Tris-HCl (pH 8.0), 10 mM of $MgCl_2$ and 1 µg of λ-DNA. One unit of nuclease equals the amount of nuclease in the assay buffer at 37° C. for 20 min that causes the disappearance of high molecular weight of λ-DNA and accumulation of 100-400 bp (around or just below the migration of the bromophenol blue dye) of low molecular weight DNA fragments on a 1% agarose gel stained with ethidium bromide. The lane with a * symbol (lane 4, FIG. 1) indicates the amount of enzyme which is defined as one unit of nuclease activity.

Cellular Fractions of E. coli Carrying pMAL-c2X-nucS

Cellular fractionations from 10 ml of induced cell culture (ER1992 as a host) were prepared as described using the spheroplast protocol (Randall and Hardy. Cell 46(6):921-8 (1986)). Two well-known enzymatic activities are used to indicate the compartments of E. coli: the presence of the β-galactosidase activity indicates the cytoplasmic fraction whereas the alkaline phosphatase activity indicates the periplasmic fraction.

Assay for β-Galactosidase Activity

β-galactosidase activity was assayed in a reaction mixture containing 180 μl of Z-buffer (0.06 M $Na_2HPO_4$/0.04M $NaH_2PO_4$, 0.1 M KCl, 0.001 M $MgSO_4$. 0.05 M β-mercaptoethanol) and 40 μl of O-nitrophenyl-β-galactoside (10 mg/ml) at 37° C. Color was monitored at 420 nm.

Assay for Alkaline Phosphatase Activity

Alkaline phosphatase activity was assayed in a reaction mixture containing 180 μl of 1 M Tris-HCl (pH 8.0) and 20 μl of 10 mM p-nitrophenylphosphate at 37° C. Color was monitored at 420 nm.

Expression of Intracellular MBP-Nuclease Fusion Protein from E. coli

The nuclease activity was predominantly present in the cell pellet and less than 0.1% of total activity was present in the medium (FIG. 2).

To further narrow down the location of S. marcescens nuclease fused to MBP, the E. coli compartments were fractionated as described previously. As shown in Table 1, cellular fractionation confirmed that most of the nuclease activity was present in the cytoplasm where more than 98% of the β-galatosidase activity is present.

TABLE 1

Cellular fractions of E. coil carrying pMAL-c2X-nucS gene

|  | Cell culture | Periplasm | cytoplasm | Total activity |
| --- | --- | --- | --- | --- |
| Alkaline Phosphatase | N.A. | 80% | 20% | 100% |
| β-galactosidase | N.A. | <2% | 98% | 100% |
| Nuclease | <0.1% | <5% | 95% | 100% |

Purification of MBP-Nuclease

MBP-nuclease fusion proteins were expressed in E. coli strains ER2683 and ER1992. 100 ml of cell culture were grown and cells were harvested by centrifugation. Cells were sonicated followed by centrifugation to remove cell debris as well as inclusion bodies. The supernatant fraction was called crude extracts thereafter. The amount of MBP-nuclease fusion in the crude extracts of these two strains did not show any difference as shown in FIG. 3, lane 2 (from ER2683) and lane 3 (from ER1992). Lane 1 is a protein marker (New England Biolabs, Inc., Ipswich, Mass., #P7702). Crude extracts were then loaded onto an amylose column; lane 4 shows the unbound fraction from ER1992 host strain; lanes 5 and 6 show the S. marcescens nuclease fused to MBP eluted by the addition of 10 mM maltose to the column. About 3.2 mg nuclease/cells were obtained from 100 ml LB broth.

Use of MBP-Nuclease Fusion for a Non-Mechanical Lysis of Bacterial Cells

MBP-nuclease fusion protein was used in conjunction with a detergent decanoyl-N-methylglucamide (MEGA-10) and chicken egg-white lysozyme. To a cell culture, CD-lysis reagent, containing 500 mM Tris-HCl (pH 7.9), 2 mM EDTA, 3% MEGA-10, 500 mM NaCl and 5% glycerol, was added directly to the cell culture to lyse cell.

For example, 100 μl of CD-lysis buffer, lysozyme (final concentration 15 μg/ml) and S. marcescens nuclease fused to MBP (1 unit) was added to 1 ml of cell culture to lyse cells prior to centrifugation.

Alternatively, 1 ml of cell culture was spun down and the pellets were resuspended in 100 μl of PR-lysis with additional of lysozyme (final concentration 150 μg/ml) and 1 unit of S. marcescens nuclease fused to MBP. The PR-lysis buffer containing 50 mM Tris-HCl (pH 7.9), 0.2 mM EDTA, 0.5% MEGA-10, 50 mM NaCl and 5% glycerol.

As shown in FIG. 5, similar amount of protein was released to extracellular environment of E. coli as determined by a Bradford protein assay, using non-mechanical methods (i.e., CD-lysis or PR-lysis reagents) or mechanical method (i.e., sonication). Two different strains of E. coli, BL21 and BL21 (DE3), were tested and both cells were lysed in a similar manner in terms of the amount of released proteins from cells.

Example II

Over-Expression of S. aureus Nuclease Fused to MBP

Bacterial Strain and Growth

The E. coli strain ER1992 was used to propagate plasmids and express fusion proteins. Plasmid pMAL-c2X (New England Biolabs, Inc., Ipswich, Mass.) was used to clone the nuclease DNA (FIG. 8a, SEQ ID NO:3) with expression controlled by $P_{tac}$ promotor and the lad repressor. Normal growth medium was LB supplemented with 100 μg/ml Amp and 0.2% (w/v) of glucose. E. coli was grown at 37° C.

Preparation of Genomic DNA

An S. aureus V8 strain was purchased from ATCC (#49775). A one ml preparation of S. aureus cells grown overnight was centrifuged and resuspended in 100 μl of $H_2O$ containing 0.2% NP-40 and 10 mM EDTA. The solution was incubated at 100° C. for 10 min to release the genomic DNA of S. aureus and to serve as a template for PCR.

Cloning of Nucleases from S. aureus

In order to amplify the nuclease by Vent DNA polymerase (New England Biolabs, Inc., Ipswich, Mass., NEB #M0254S), two primers were synthesized: 5'-GCAACT-TCAACTAAAAAATTACATAAAGAACC-3' (SEQ ID NO:7) and 5'-TTAAGGATCCTTATTGACCTGAAT-CAGCGTTGTCTTC-3' (SEQ ID NO:8). The PCR product was 450 bp and was cut with BamHI. Gel-purified BamHI-cut PCR products were kinased and cloned into the XmnI/BamHI region of pMAL-c2X vector, followed by transforming into ER1992. Six out of 40 colonies were found to carry the nuclease activity according to the assay below. The isolated plasmids containing the nuclease gene were sequenced using the ABI Bigdye terminator V3.1 sequencing kit (Applied Biosystems, Foster City, Calif.). DNA sequence confirmed that six of the clones carry the gene of S. aureus nuclease. This plasmid was named pMAL-c2X-nuclease(S7) (S7 for S. aureus).

New transformants (ER1992) carrying pMAL-c2X-nuclease(S7) plasmid were grown at 37° C. on an LB plate with Amp. A single colony was inoculated into 2 ml LB+glucose and grown overnight. Two hundred microliters of overnight cells were added to fresh 10 ml of LB+Amp+glucose medium and were grown until $OD_{600nm}$ reached 1.0, followed by addition of 1 mM of IPTG. After two hours induction, cells were harvested by centrifugation.

Assay for Nuclease Activity

The nuclease activity assay buffer used here contains 50 mM Tris-HCl (pH 8.0), 10 mM of $CaCl_2$ and 1 μg of λ-DNA. DNA nuclease activity can be visualized by the disappearance of high molecular weight of λ-DNA and accumulation of 100-400 bp (around or just below the migration of the bromophenol blue dye) of low molecular weight DNA fragments on a 1% agarose gel stained with ethidium bromide (FIG. 6).

Expression of Intracellular *S. aureus* Nuclease Fused to MBP and Purification from *E. coli*

*S. aureus* nuclease fused to MBPs were expressed in ER1992 hosts. 10 ml of cell culture were grown in LB medium and IPTG-induced cells were harvested by centrifugation. Cell pellets were resuspended in 50 mM Tris-HCl (pH 7.5)/50 mM NaCl buffer followed by sonication. Cell debris was spun down and the crude extracts, where the DNA nuclease activity was found (FIG. 6, lane 1-5), were then loaded onto an amylose column. As shown on FIG. 7, lane 1 is the protein marker (New England Biolabs, Inc., Ipswich, Mass., #P7702), lane 2 shows the crude extracts, lane 3 shows the *S. aureus* nuclease fused to MBP eluted by the addition of 10 mM maltose to the column. Purified *S. aureus* nuclease fused to MBP DNase activity was shown on FIG. 6 (lane 6-10). Hence, it was concluded that the *S. aureus* nuclease fused to MBP was expressed as a soluble form in the cell.

---

What is claimed is:

1. A DNA segment encoding a recombinant fusion protein containing maltose-binding protein fused to a nuclease comprising SEQ ID NO: 2 or SEQ ID NO: 4.

2. A host cell comprising a DNA segment encoding a recombinant fusion protein containing maltose-binding protein fused to a nuclease comprising SEQ ID NO: 2 or SEQ ID NO: 4.

3. A method for obtaining a nuclease, comprising:
   (a) obtaining a DNA segment encoding a recombinant fusion protein containing maltose-binding protein fused to a nuclease comprising SEQ ID NO: 2 or SEQ ID NO: 4;
   (b) expressing the DNA segment within a host cell to produce the fusion protein in the cytoplasm;
   (c) lysing the host cell; and
   (d) obtaining the isolated nuclease.

4. The method of claim 3, wherein the nuclease comprises SEQ ID NO: 2.

5. The method of claim 3, wherein the nuclease comprises SEQ ID NO: 4.

6. The DNA segment of claim 1, wherein the nuclease comprises SEQ ID NO: 2.

7. The DNA segment of claim 1, wherein the nuclease comprises SEQ ID NO: 4.

8. The host cell of claim 2, wherein the nuclease comprises SEQ ID NO: 2.

9. The host cell of claim 2, wherein the nuclease comprises SEQ ID NO: 4.

* * * * *

SEQUENCE LISTING

<160> NUMBER OF SEQ ID NOS: 8

<210> SEQ ID NO 1
<211> LENGTH: 1902
<212> TYPE: DNA
<213> ORGANISM: unknown
<220> FEATURE:
<223> OTHER INFORMATION: non-secreted form of Serratia marcescens
      nuclease fused to maltose-binding protein

<400> SEQUENCE: 1

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt atcgctgat ttataacaaa      360 gatctgctgc cgaacccgcc aaaaacctgg aagagatcc cggcgctgga taagaactg      420 aaagcgaaag taagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga agatccacg tattgccgcc     960 actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa    1080 gccctgaaag acgcgcagac taattcgagc tcgaacaaca acaacaataa caataacaac    1140
aacctcggga tcgagggaag ggccgacacg ctcgaatcca tcgacaactg cgcggtcggc    1200
tgtccgaccg gcggcagcag caacgtgtct atcgtgcgtc atgcttatac gttgaacaac    1260
aacagcacca ccaagttcgc caactgggtg gcctatcaca tcaccaaaga cacgccggcc    1320
agcggcaaga cgcgcaactg gaaaaccgat ccggcgctca acccgcgcga tacgttggcg    1380
cccgccgatt acaccggcgc caacgccgcg ctgaaggtcg atcgcggtca tcaggcgccg    1440
```

```
ctggcctcgc tggcgggcgt ctccgactgg gaatcgttga actacctgtc caacatcacg    1500
ccgcaaaagt ccgatctgaa ccagggcgcc tgggcgcggc tggaagatca ggaacgcaag    1560
ctgatcgatc gcgccgatat atcctcggtc tataccgtga ccgggccgct gtatgagcgc    1620
gatatgggca aactgccggg cacgcagaaa gcgcacacca tccccagcgc ctactggaag    1680
gtgattttca tcaacaacag cccggcggtg aaccactatg ccgccttcct gttcgaccag    1740
aacacgccga agggcgccga tttctgccaa ttccgcgtga cggtggacga gatcgagaaa    1800
cgcaccggcc tgatcatctg gccggtctg ccggacgacg tgcaggcttc gctgaagagc    1860
aaaccgggcg ttctgccgga gttgatgggc tgcaaaaact ga                      1902

<210> SEQ ID NO 2
<211> LENGTH: 633
<212> TYPE: PRT
<213> ORGANISM: unknown
<220> FEATURE:
<223> OTHER INFORMATION: non-secreted form of Serratia marcescens
      nuclease fused to maltose-binding protein

<400> SEQUENCE: 2

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270
```

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
                    340                 345                 350

Ser Gly Arg Gln Thr Val Asp Glu Ala Leu Lys Asp Ala Gln Thr Asn
                    355                 360                 365

Ser Ser Ser Asn Asn Asn Asn Asn Asn Asn Asn Leu Gly Ile
                    370                 375                 380

Glu Gly Arg Ala Asp Thr Leu Glu Ser Ile Asp Asn Cys Ala Val Gly
385                 390                 395                 400

Cys Pro Thr Gly Gly Ser Ser Asn Val Ser Ile Val Arg His Ala Tyr
                    405                 410                 415

Thr Leu Asn Asn Asn Ser Thr Thr Lys Phe Ala Asn Trp Val Ala Tyr
                    420                 425                 430

His Ile Thr Lys Asp Thr Pro Ala Ser Gly Lys Thr Arg Asn Trp Lys
                    435                 440                 445

Thr Asp Pro Ala Leu Asn Pro Ala Asp Thr Leu Ala Pro Ala Asp Tyr
450                 455                 460

Thr Gly Ala Asn Ala Ala Leu Lys Val Asp Arg Gly His Gln Ala Pro
465                 470                 475                 480

Leu Ala Ser Leu Ala Gly Val Ser Asp Trp Glu Ser Leu Asn Tyr Leu
                    485                 490                 495

Ser Asn Ile Thr Pro Gln Lys Ser Asp Leu Asn Gln Gly Ala Trp Ala
                    500                 505                 510

Arg Leu Glu Asp Gln Glu Arg Lys Leu Ile Asp Arg Ala Asp Ile Ser
                    515                 520                 525

Ser Val Tyr Thr Val Thr Gly Pro Leu Tyr Glu Arg Asp Met Gly Lys
                    530                 535                 540

Leu Pro Gly Thr Gln Lys Ala His Thr Ile Pro Ser Ala Tyr Trp Lys
545                 550                 555                 560

Val Ile Phe Ile Asn Asn Ser Pro Ala Val Asn His Tyr Ala Ala Phe
                    565                 570                 575

Leu Phe Asp Gln Asn Thr Pro Lys Gly Ala Asp Phe Cys Gln Phe Arg
                    580                 585                 590

Val Thr Val Asp Glu Ile Glu Lys Arg Thr Gly Leu Ile Ile Trp Ala
                    595                 600                 605

Gly Leu Pro Asp Asp Val Gln Ala Ser Leu Lys Ser Lys Pro Gly Val
610                 615                 620

Leu Pro Glu Leu Met Gly Cys Lys Asn
625                 630

<210> SEQ ID NO 3
<211> LENGTH: 1611
<212> TYPE: DNA
<213> ORGANISM: unknown
<220> FEATURE:
<223> OTHER INFORMATION: non-secreted form of Staphylococcus aureus
      nuclease fused to maltose-binding protein

<400> SEQUENCE: 3

```
atgaaaatcg aagaaggtaa actggtaatc tggattaacg gcgataaagg ctataacggt    60
ctcgctgaag tcggtaagaa attcgagaaa gataccggaa ttaaagtcac cgttgagcat   120
ccggataaac tggaagagaa attcccacag gttgcggcaa ctggcgatgg ccctgacatt   180
atcttctggg cacacgaccg ctttggtggc tacgctcaat ctggcctgtt ggctgaaatc   240
accccggaca aagcgttcca ggacaagctg tatccgttta cctgggatgc cgtacgttac   300
aacggcaagc tgattgctta cccgatcgct gttgaagcgt atcgctgat ttataacaaa    360
gatctgctgc cgaacccgcc aaaaacctgg aagagatcc cggcgctgga taagaactg     420
aaagcgaaag gtaagagcgc gctgatgttc aacctgcaag aaccgtactt cacctggccg   480
ctgattgctg ctgacggggg ttatgcgttc aagtatgaaa acggcaagta cgacattaaa   540
gacgtgggcg tggataacgc tggcgcgaaa gcgggtctga ccttcctggt tgacctgatt   600
aaaaacaaac acatgaatgc agacaccgat tactccatcg cagaagctgc ctttaataaa   660
ggcgaaacag cgatgaccat caacggcccg tgggcatggt ccaacatcga caccagcaaa   720
gtgaattatg gtgtaacggt actgccgacc ttcaagggtc aaccatccaa accgttcgtt   780
ggcgtgctga gcgcaggtat taacgccgcc agtccgaaca aagagctggc aaaagagttc   840
ctcgaaaact atctgctgac tgatgaaggt ctggaagcgg ttaataaaga caaaccgctg   900
ggtgccgtag cgctgaagtc ttacgaggaa gagttggcga agatccacg tattgccgcc    960
actatggaaa acgcccagaa aggtgaaatc atgccgaaca tcccgcagat gtccgctttc  1020
tggtatgccg tgcgtactgc ggtgatcaac gccgccagcg gtcgtcagac tgtcgatgaa  1080
gccctgaaag acgcgcagac taattcgagc tcaacaaca caacaataa caataacaac   1140
aacctcggga tcgagggaag ggcaacttca actaaaaaat tacataaaga acctgcgaca  1200
ttaattaaag cgattgatgg tgatactgtt aaattaatgt acaaaggtca accaatgaca  1260
ttcagactat tattggttga tacacctgaa acaaagcatc ctaaaaaagg tgtagagaaa  1320
tatggtcctg aagcaagtgc atttacgaaa aagatggtag aaaatgcaaa gaaaattgaa  1380
gtcgagtttg acaaaggtca aagaactgat aaatatggac gtggcttagc gtatatttat  1440
gctgatggaa aaatggtaaa cgaagcttta gttcgtcaag gcttggctaa agttgcttat  1500
gtttataaac ctaacaatac acatgaacaa cttttaagaa aaagtgaagc acaagcgaaa  1560
aaagagaaat taaatatttg gagcgaagac aacgctgatt caggtcaata a           1611
```

<210> SEQ ID NO 4
<211> LENGTH: 536
<212> TYPE: PRT
<213> ORGANISM: unknown
<220> FEATURE:
<223> OTHER INFORMATION: non-secreted form of Staphylococcus aureus nuclease fused to maltose-binding protein

<400> SEQUENCE: 4

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60
```

-continued

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
            85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Asn Leu Gly Ile
            370                 375                 380

Glu Gly Arg Ala Thr Ser Thr Lys Lys Leu His Lys Glu Pro Ala Thr
385                 390                 395                 400

Leu Ile Lys Ala Ile Asp Gly Asp Thr Val Lys Leu Met Tyr Lys Gly
            405                 410                 415

Gln Pro Met Thr Phe Arg Leu Leu Leu Val Asp Thr Pro Glu Thr Lys
            420                 425                 430

His Pro Lys Lys Gly Val Glu Lys Tyr Gly Pro Glu Ala Ser Ala Phe
            435                 440                 445

Thr Lys Lys Met Val Glu Asn Ala Lys Lys Ile Glu Val Glu Phe Asp
            450                 455                 460

Lys Gly Gln Arg Thr Asp Lys Tyr Gly Arg Gly Leu Ala Tyr Ile Tyr
465                 470                 475                 480

Ala Asp Gly Lys Met Val Asn Glu Ala Leu Val Arg Gln Gly Leu Ala
            485                 490                 495

-continued

```
Lys Val Ala Tyr Val Tyr Lys Pro Asn Asn Thr His Glu Gln Leu Leu
            500                 505                 510
Arg Lys Ser Glu Ala Gln Ala Lys Glu Lys Leu Asn Ile Trp Ser
        515                 520                 525
Glu Asp Asn Ala Asp Ser Gly Gln
        530                 535

<210> SEQ ID NO 5
<211> LENGTH: 27
<212> TYPE: DNA
<213> ORGANISM: unknown
<220> FEATURE:
<223> OTHER INFORMATION: primer

<400> SEQUENCE: 5
gccgacacgc tcgaatccat cgacaac                                    27

<210> SEQ ID NO 6
<211> LENGTH: 37
<212> TYPE: DNA
<213> ORGANISM: unknown
<220> FEATURE:
<223> OTHER INFORMATION: primer

<400> SEQUENCE: 6
agtcggatcc tcagtttttg cagcccatca actccgg                         37

<210> SEQ ID NO 7
<211> LENGTH: 32
<212> TYPE: DNA
<213> ORGANISM: unknown
<220> FEATURE:
<223> OTHER INFORMATION: primer

<400> SEQUENCE: 7
gcaacttcaa ctaaaaaatt acataaagaa cc                              32

<210> SEQ ID NO 8
<211> LENGTH: 37
<212> TYPE: DNA
<213> ORGANISM: unknown
<220> FEATURE:
<223> OTHER INFORMATION: primer

<400> SEQUENCE: 8
ttaaggatcc ttattgacct gaatcagcgt tgtcttc                         37
```